(12) United States Patent
Docherty

(10) Patent No.: US 7,037,945 B2
(45) Date of Patent: May 2, 2006

(54) **METHOD OF INHIBITING FORMATION OF *NEISSERIA GONORRHEA* AND *NEISSERIA MENINGIDITIS***

(75) Inventor: John Docherty, Kent, OH (US)

(73) Assignee: Northeastern Ohio Universities College of Medicine, Rootstown, OH (US)

( * ) Notice: Subject to any disclaimer, the term of this patent is extended or adjusted under 35 U.S.C. 154(b) by 0 days.

(21) Appl. No.: 10/013,760

(22) Filed: Dec. 11, 2001

(65) Prior Publication Data

US 2006/0035984 A1    Feb. 16, 2006

Related U.S. Application Data

(63) Continuation of application No. 09/734,444, filed on Dec. 11, 2000, now Pat. No. 6,355,692.

(51) Int. Cl.
*A01N 31/08*    (2006.01)
*A61K 31/05*    (2006.01)

(52) U.S. Cl. .................. 514/733; 514/734; 514/736

(58) Field of Classification Search ............. 514/733, 514/734, 736
See application file for complete search history.

(56) References Cited

U.S. PATENT DOCUMENTS 5,500,367 A * 3/1996 Hain et al. ............ 435/252.3
6,022,901 A * 2/2000 Goodman ................ 514/733
6,197,834 B1   3/2001 Docherty ................ 514/733

OTHER PUBLICATIONS

Mahady et al, Am. J. of Gastroenterology, vol. 95, Jul. 2000, p. 1849.*
Adesanya et al, 111CA:171177, 1989.*
Lysko et al, 93CA:215955, 1980.*
Anne, et al, 94CA:57949, 1980.*
Miura et al. "Antioxidative and Prooxidative Action of Stilbene Derivatives" 2000, Pharmacology & Toxicology, 86, 203-208.*
Pathan et al. "Pathophysiology of meningococcal meningitis and septicaemia" 2003, Arch Dis Child, 88, 601-607.*
Zheng et al. "Antimicrobial susceptibility of *Neisseria gonorrhoeae* strains isolated in Guangzhou, China 1996-2001" 2003, Sex Transm Infect, 79, 399-402.*

"Antibacterial Constituents of *Ficus Barteri* Fruits" by Ogungbamila, et al., *International Journal of Pharmacognosy*, vol. 35, No. 3, 1997, pp. 185-189.
"Resveretrol Inhibits the Growth of *Helicobacter pyloir* in Vitro" by Mahady, et al., *American Journal of Gastroenterology*, 95:1849, Jul. 2000.
"Resveretrol selectively inhibits *Neisseria gonorrhoeae* and *Neisseria meningitidis*" by Docherty, et al., *Journal of Antimicrobial Chemotherapy*, 47:243-244, Feb., 2001.
"Oxidative Stress During Viral Infection: A Review" by Schwarz, *Free Radical Biology & Medicine*, vol. 21, No. 5, pp. 641-649, 1996.
"Effect of Stilbene Derivatives on Gastric $H^+$, $K^+$-ATPase" by Murakami, et al., *Biochemical Pharmacology*, vol. 44, No. 10, pp. 1947-1951, 1992.
"Antioxidants Selectively Suppress Activation of NF-κB by Human T-Cell Leukemia Virus Type 1 Tax Protein" by Schreck, et al., *Journal of Virology*, vol. 66, No. 11, Nov. 1992, pp. 6288-6293.
"Resveretrol Arrests the Cell Division Cycle at S/G2 Phase Transition" by Ragione, et al., *Biochemical and Biophysical Research Communication*, 250, 53-58 (1998).
"Cancer Chemopreventive Activity of Resveretrol, a Natural Product Derived from Grapes" by Jang, et al., *Science*, vol. 275, Jan. 10, 1997, pp. 218-220.
"Resveretrol: A Molecule Whose Time Has Come? And Gone?" by Soleas, et al., *Clinical Biochemistry*, vol. 30, No. 2, Mar. 1997, pp. 91-113.
"Evaluation of antioxidant healing formulations in topical therapy of experimental cutaneous and genital herpes simplex viral infections" by Sheridan, et al., *Antiviral Research*, 36 (1997) 157-166.

(Continued)

*Primary Examiner*—Sreeni Padmanbhan
*Assistant Examiner*—Gregory W Mitchell
(74) *Attorney, Agent, or Firm*—Calfee, Halter & Griswold LLP

(57) ABSTRACT

The present invention provides a method of inhibiting the formation of pseudorabies particles in a host cell. The method involves administering an effective amount of a poly-hydroxylated stilbene, particularly resveratrol, to a herpes virus infected host cell. The present invention also provides a method of reducing or inhibiting the growth of *Neisseria gonorrhea* and *Neisseria meningiditis* in vitro and in vivo. The method comprises administering a composition comprising a therapeutically effective amount of a tri-hydroxylated stilbene to a growth surface which has come into contact or could come into contact with the bacterium.

10 Claims, 1 Drawing Sheet

OTHER PUBLICATIONS

"Resveretrol, a remarkable inhibitor of ribonucleotide reductase" by Fontecave, et al., *FEBS Letters*, 421 (1998) 277-279.

"Effect of diethylstilbestrol on replication and transformation by human herpes viruses" by Rapp, et al., *Intervirology* (1979), 12(2), 103.

* cited by examiner

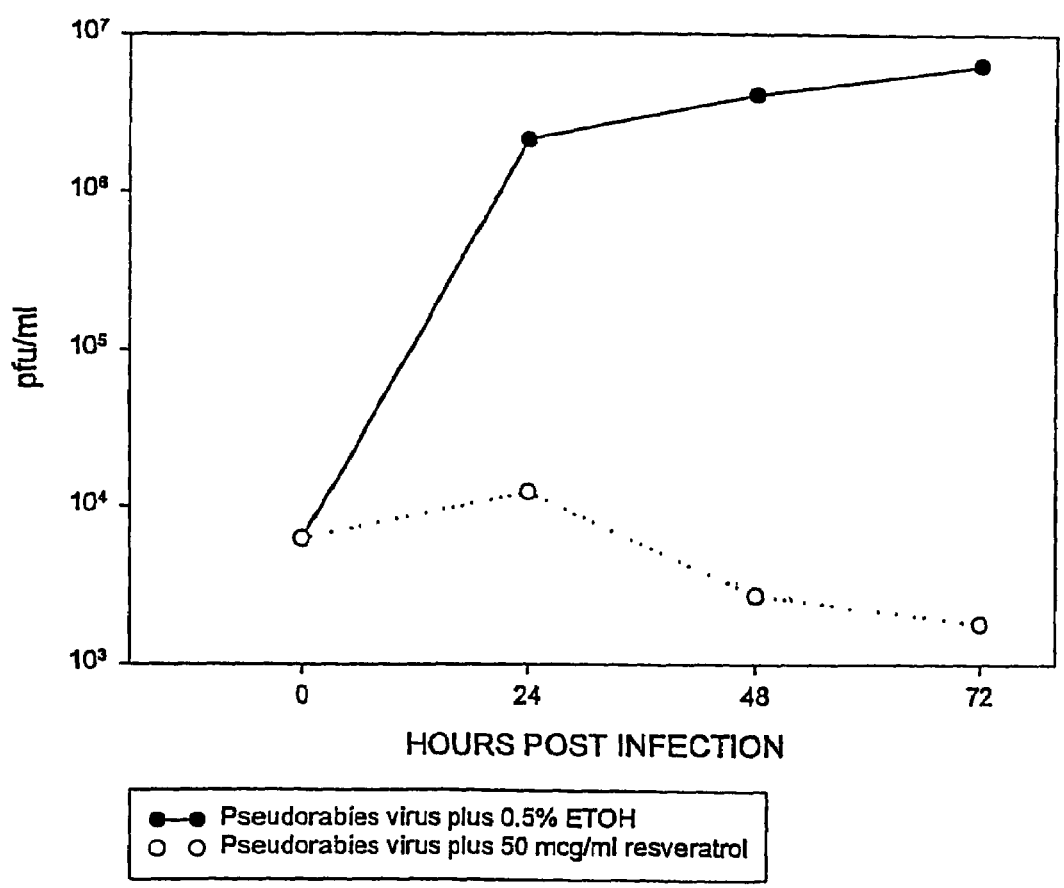

METHOD OF INHIBITING FORMATION OF NEISSERIA GONORRHEA AND NEISSERIA MENINGIDITIS

CROSS-REFERENCE TO RELATED APPLICATIONS

This application is a continuation of the commonly assigned, U.S. Patent application Ser. No. 09/734,444, filed on Dec. 11, 2000 issued as U.S. Pat. No. 6,355,692.

BACKGROUND

The present invention relates to methods of inhibiting replication of three pathogenic microorganisms, pseudorabies virus, *Neisseria gonorrheae*, and *Neisseria meningiditis*.

Pseudorabies virus, a member of the Herpesvirus family, primarily affects swine. Because virus is present in the nasal and oral discharges of infected pigs, infection is usually transmitted between pigs by none to nose contact. Contaminated drinking water and feed buckets may also transmit disease. Clinical symptoms in pigs can vary from undetectable to death. The extent of the symptoms depends on the age and immune status of the animal at the time of infection, the virus dose, route of infection, and strain of virus. Young pigs may be severely affected with a 100% mortality in pigs under 2 weeks of age. Piglets may die suddenly or, prior to death, exhibit symptoms which include fever, loss of appetite, convulsions, and paddling. The severity of clinical signs decreases with age, and older pigs may only experience fever and inappetence of a few days duration.

Since pseudorabies is a virus infection, antibiotics have no effect. The primary methods for preventing spread of the disease involves treatment of environmental surfaces with agents that inactivate the virus. Examples of such agents are phenolic compounds, quaternary ammonimum compounds, chlorhexidine diacetate, iodines, and 5% sodium hydroxide. Vaccines may also be used to control spread of the disease. Additional methods for inhibiting replication of the virus, and thereby controlling the spread of the virus and the severity of the disease in swine exposed to the virus are desirable.

*Neisseria gonorrhea* is a gram negative bacterium that is pathogenic in humans. The bacterium is spread from person to person by contact with infected secretions, most often by sexual contact. Once the pathogen is deposited on a mucosal surface, a complex series of molecular interactions occur that result in invasion of mucosal columnar cells. The spectrum of diseases ranges from local infections of the urethral, cervical, rectal and oropharyngeal membranes to invasion of the pelvis or epididymis, to invasion of the blood stream, with or without dissemination to distant organs such as heart valves, joints, and pericardium. The pathogen may also infect the conjunctiva. Gonococcal conjunctivitis is most often contracted by neonates passing through an infected birth canal, although adults can also be infected.

The quest for a gonococcal vaccine has been ongoing for many years with virtually no success. Accordingly, the primary treatment involves preexposure or postexposure antibiotic prophylaxis. In addition to antibiotic eyedrops, silver nitrate has also been used to treat neonatal gonococcal conjunctivitis. Unfortunately, the bacterium has developed resistance to some of the most common antibiotics, such as penicillin. Accordingly, additional compositions for reducing growth of this pathogen is desirable.

*Neisseria meningiditis*, another member of the genus *Neisseria*, is also pathogenic in humans. The organism is carried on the nasopharyngeal mucosa of infected individuals and, presumably, is transmitted from person to person through passage of respiratory secretions or aeosolized droplets. Although the organism may cause oropharyngitis, it is primarily a saprophyte that asymptomatically colonizes the majority of human beings sometime during their lives. As with other neisserial species, it can sometimes colonize the genital tract or conjunctiva. On rare occasions, the organism invades the blood stream. Once the organism has invaded the blood stream, an overlapping array of clinical outcomes ranging from a transient bacteremia, to invasion of the meninges, and encephalitis can occur. Treatment primarily involves administration of antibiotics. Vaccines are also used to prevent infection. Unfortunately, the bacterium may develop resistance to the antibiotics. Moreover, the duration of immunity with the currently available vaccines is limited. Accordingly, it is desirable to have new methods for preventing or inhibiting growth of *Neisseria meningiditis*.

SUMMARY OF THE INVENTION

The present invention provides a new method of inhibiting the formation of infectious pseudorabies virus particles, in a host cell. The method involves administering a poly-hydroxylated stilbene, particularly resveratrol, or a derivative thereof to a pseudorabies virus infected host cell. The poly-hydroxylated stilbene is administered to the host cell in an amount sufficient to inhibit replication of the virus in the virus-infected host cell. Such method is useful for preventing the spread of pseudorabies virus from a virus-infected host cell to a non-infected host cell. Such method is also useful for establishing a model system for studying the molecular events that occur during replication of pseudorabies virus. In vivo, the method involves administering a composition comprising a poly-hydroxylated stilbene, preferably a tri-hydroxylated stilbene, or a derivative thereof to a non-human animal prior to or shortly after exposure of the animal to the virus. Such method is useful for reducing the cytopathic effect of a pseudorabies virus infection.

The present invention also provides a method of inhibiting replication of the gram negative bacteria belonging to the genus *Neisseria*, particularly *Neisseria gonorrhea* and *Neisseria meningiditis*. Such method involves contacting the bacterium with a composition containing a tri-hydroxylated stilbene or derivative thereof. In vivo, such method can be used to treat an individual who has come in contact with, e.g., a carrier, or an individual who is expected to come into contact with the bacterium, i.e., an individual who may be exposed to the carrier. In vivo, such method comprises administering a composition comprising a therapeutically effective amount of a tri-hydroxylated stilbene, particularly resveratrol, or a derivative thereof to said subject.

BRIEF DESCRIPTION OF THE FIGURES

FIG. 1 is a graph showing the extent of pseudorabies virus replication in virus-infected cells incubated in medium lacking resveratrol or containing 50 μg/ml of resveratrol.

DETAILED DESCRIPTION OF THE INVENTION

In accordance with the present invention, it has been discovered that tri-hydroxylated stilbenes, particularly resveratrol has an antimicrobial effect on select pathogenic microorganisms including pseudorabies virus, *Neisseria gonorrhea*, and *Neisseria meningiditis*.

In accordance with the present invention, it has also been shown that resveratrol at concentrations ranging from 1 µg/ml to 200 µg/ml of solution does not inhibit the growth of *Eschericia coli*, *Staphylococcu aureus*, Group A beta-hemolytic *Streptococcus*, *Pseudomonas aeruginosa* or *Candida albicans*.

Tri-Hydroxylated Stilbenes

The structural skeleton of the compound employed in the present methods, i.e., the polyhydroxylated stilbene, comprises two aromatic rings joined by an ethylene bridge. Preferably, the compound is a tri-hydroxystilbene, more preferably 3,5,4'-trihdyroxystilbene, which is also known as resveratrol, or a derivative thereof. Resveratrol in either the cis form or trans form is suitable. Derivatives of resveratrol as used herein refers to compounds in which one or two of the hydroxyl functions of resveratrol are replaced with other moieties such as, for example, pterostilbene in which the hydroxyl functions at positions 3 and 5 on the disubstituted aromatic ring are methoxylated. Another example is β-glucoside derivative polydatin or piceid, in which one of the hydroxyl functions on the disubstituted aromatic ring is replaced with glucose; as well as polymers of the parent compound resveratrol. Such polymers have been given the name viniferins. Methods for producing the hydroxylated stilbenes are described in Moreana-Manas, M. et al, Anal Quim (1985) 81:157–161; Jeandet, P. et al, Am J. Enol Vitic (1991) 42:41–6; Goldberg DM et al. Anal Chem (1994) 66:3959–63, Murakami, S et al, Biochem Pharmacol. (1992) 44:1947–51; and Thakkar, K et al, J. Med Chem (1993) 36:2650–51, which are incorporated herein by reference. Resveratrol and 3,3',4,5'-tetrahydroxy-trans-stilbene, known as piceatoannol, are also available commercially from Sigma Chemical Co., St. Louis, Mo.

Methods of Inhibiting Formation of Infectious Pseudorabies Viral Particles

In one aspect, the present invention provides a method of inhibiting formation of infectious pseudorabies viral particles in a host cell. The method comprises administering a polyhydroxylated stilbene, preferably a tri-hydroxylated stilbene, or a derivative thereof to the host cell. The polyhydroxylated stilbene is administered in an amount sufficient to or effective to inhibit replication of the pseudorabis virus within the infected cell. Preferably, the polyhydroxylated stilbene or derivative thereof is administered to the host cell either prior to infection of the host cell with the virus or preferably, within six hours after infection of the host cell with the virus.

Preferably, the tri-hydroxylated stilbene or derivative thereof is administered to the host cell by contacting the host cell with or exposing the host cell to a composition comprising the tri-hydroxylated stilbene or derivative thereof. For example, in vitro, the method comprises adding a tri-hydroxylated stilbene to the culture medium of pseudorabies virus-infected host cells. In the case of cultured cells, the tri-hydroxylated stilbene is added to the medium, preferably before the host cells are infected with the virus or within six hours after the host cells are infected with the virus. Good results have been obtained by exposing cultured host cells to the tri-hydroxylated stilbene, resveratrol, at a concentration which is greater than 1 µg/ml and less than 200 µg/ml of culture medium.

It has been determined that treatment of cultured cells in accordance with the present method is non-toxic to cells and blocks replication of pseudorabies virus at some early stage in it replicative cycle. It has also been determined that the effect of resveratrol on pseudorabies virus replication is reversible. Typical of the herpes viruses, pseudorabies replication occurs in phases, with each phase being dependent on the successful completion of the prior phase. The "immediate early phase" occurs at 1–3 hours after infection and is associated with regulatory and synthetic events. The "early phase" occurs 3–6 hours after infection and is also associated with regulatory and synthetic events, particularly the synthesis of virus DNA. The "late phase" occurs 6–10 hours after infection and is associated with final synthetic events and assembly of viral components into infections virions. Such method is useful for establishing model systems for studying the molecular events that occur during replication of pseudorabies virus. For example, mammalian cell cultures incubated in the presence and absence of resveratrol may be used to identify cellular factors that are involved in regulating pseudorabies virus synthetic events. Such cell cultures may also be employed to characterize the role of psuedorabies virus gene products in the replication of infectious virus, particularly those proteins and factors whose function are currently unknown.

In vivo, the method is used to inhibit the development of or to reduce the severity of a pseudorabies infection in a mammalian subject, particularly a non-human mammalian subject. Such method comprises administering a therapeutically effective amount of the tri-hydroxylated stilbene or derivative thereof to a mammalian subject prior to or shortly after exposure to the virus. Such method is particularly useful for reducing the severity of infection in a pig and, in some cases, preventing the animal from becoming a carrier. Since transmission among pigs is typically due to nose to nose contact, it is preferred that the tri-hydroxylated stilbene be administered in a composition which enters the pig through the nose or the oropharynx. For example, the tri-hydroxylated stilbene may be added to the drinking water or the feed of animals that may have come into contact with or could come into contact with the virus. In addition, the tri-hydroxylated stilbene may be incorporated into an aerosolizable solution or suspension which is then misted into the nurseries of newborn piglets.

Method of Inhibiting Growth of *Neisseria gonorrheae* or *Neisseria meningiditis*

In another aspect, the present invention provides a method of inhibiting the growth of *Neisseria gonnorhea* and *Neisseria meningiditis*. The method comprises administering a tri-hydroxylated stilbene, preferably resveratrol, or a derivative thereof to a surface which has come in contact with or could come in contact with the organism. In vivo, the method, which comprises administering the tri-hydroxylated stilbene to a mucous membrane of a human subject, may be used to prevent or reduce the symptoms of gonnococcal or meningococcal disease in the human subject. The tri-hydoxylated stilbene or derivative thereof may be incorporated into a pharmaceutical composition which is applied to the mucous membrane of a carrier of the bacterium or a person who could come into contact with the carrier.

Pharmaceutical compositions used in the present methods comprise a therapeutically effective amount of a tri-hydroxylated stilbene preferably resveratrol or a derivative thereof, and a pharmaceutically acceptable carrier. Preferably, the composition comprises a relatively inert carrier. Many such carriers are routinely used and can be identified by reference to pharmaceutical texts. Examples include polyethylene glycols, polypropylene copolymers, and some water soluble gels. Such a composition may also contain diluents, fillers, salts, buffers, stabilizers, solubilizers, and other pharmaceutically acceptable materials well known in the art. The term "pharmaceutically acceptable" means a non-toxic material that does not interfere with the effectiveness of the anti-microbial activity of the tri-hydroxylated stilbene or derivative thereof.

In practicing the present method, a pharmaceutical composition comprising a therapeutically effective amount of the hydroxylated stilbene, preferably resveratrol, is applied to a potential or actual site of infection in the host subject before or after the host subject is exposed to the bacterium. Such composition may be used prophylactically to prevent or reduce the severity of infections of the eye, nose, mouth, throat, oropharynx, genitalia, and rectum. In the case of oral administration, dentrifices, mouthwashes, tooth paste or gels, or mouth sprays are used. Vaginal or rectal administration may be by the usual carriers such as douches, foams, creams, ointments, jellies, and suppositories, the longer lasting forms being preferred. Ocular administration is preferably by ophthalmic ointments or solutions.

The pharmaceutical composition may further contain other agents which either enhance the activity of the tri-hydroxylated stilbene or complement its activity or use in inhibiting growth of the gonoccocus or meningococcus. Such additional factors and/or agents may be included in the pharmaceutical composition to produce a synergistic effect with the tri-hydroxylated stilbene, or to minimize side effects.

Preferably the pharmaceutical composition comprises a solvent for the tri-hydroxylated stilbene or derivative thereof, such as, for example, an alcohol. A liquid carrier such as water, petroleum, oils of animal or plant origin such as peanut oil, mineral oil, soybean oil, or sesame oil, corn oil, or synthetic oils may be added. The liquid form of the pharmaceutical composition may further contain a physiological saline solution, dextrose or other saccharide solution, or glycols such as ethylene glycol, propylene glycol or polyethylene glycol. The preparation of such pharmaceutical composition having suitable pH, isotonicity, and stability, is within the skill in the art.

Administration of the pharmaceutical composition to an uninfected subject is via local administration to a site which has been or may be contacted with the pathogenic organism. It is preferred that the pharmaceutical composition be applied prior to exposure to the targeted pathogen or preferably within 1–24 hours, more preferably within 1–12 hours after exposure of the uninfected subject to the pathogenic organsim.

Administration of the pharmaceutical composition to a carrier of *Neisseria meningiditis* is via local administration to the upper respiratory tract, i.e. ororpharynx. Administration of the pharmaceutical composition to a carrier of *Neisseria gonorrhea* is via local administration to the genitalia, rectum, or oropharynx.

Dosage

The tri-hydroxylated stilbene, preferably resveratrol or a derivative thereof is administered to the host subject in a therapeutically effective amount. As used herein, the term "therapeutically effective amount" means the total amount of the tri-hydroxylated stilbene that is sufficient to show a meaningful benefit, i.e., prevention or reduction in the extent of infection by the targeted pathogen or a reduction in the severity of the symptoms that result from infection with the targeted pathogen. The dosages of the tri-hydroxylated stilbene, particularly resveratrol, which can prevent or reduce the severity of an infection with pseudorabies virus, *Neisseria gonorrhea* or *Neisseria meningididtis* can be determined in view of this disclosure by one of ordinary skill in the art by running routine trials with appropriate controls. Comparison of the appropriate treatment groups to the controls will indicate whether a particular dosage is effective in preventing or reducing the severity of the infection at the levels used in a controlled challenge.

It is contemplated that the various compositions used to practice the method of the present invention should contain about 0.01 μg to about 10 μg, more preferably about 0.1 μg to about 1 mg, of the tri-hydroxylated stilbene, most preferably from about 10 μg to about 100 μg of resveratrol per/ml of the composition. Although a single administration of the composition may be sufficient to ameliorate the pathological effects of the virus or bacteria, it is expected that multiple doses will be preferred.

The following examples of methods of using resveretrol to block formation of infectious psuedorabies virus particles and growth of *Neisseria gonorrhea* and *Neisseria meningiditis* in vitro are for purposes of illustration only and are not intended to limit the scope of the claims which are appended hereto.

EXAMPLE 1

Inhibiting Formation of Infectious Pseudorabies Particles by Treatment with Resveratrol Cultures of African green monkey kidney cells (Vero) cells, obtained from the American Type Culture Collection, Rockville, Md., were grown to confluence in Medium 199 supplemented with 5% fetal bovine serum, 0.075% $NaHCO_3$, and 50 μg/ml gentamycin sulfate in 25 $cm^2$ tissue culture flasks. Cells were infected with pseudorabies virus at a multiplicity of infection (moi) of one and incubated at room temperature for one hour to allow for virus attachment to and penetration of the cell. Under these conditions, approximately half of the cells are infected with virus. Thereafter, the cultures were rinsed three time with media and incubated in medium containing resveratrol at a final concentration of 50 μg/ml. Stock solutions of the resveratrol, obtained from Sigma Chemical Co, St. Louis, Mo. were prepared in 100% ethanol and diluted to the final concentration in tissue culture media. The maximum concentration of alcohol in the medium was 0.5%. Controls were treated identically, but were incubated without resveratrol.

Upon addition of the medium to the cultures and at 24 hours time periods thereafter, i.e., 0 hours, 24 hours, 48 hours, and 72 hours after addition of the drug, cells and medium were frozen at –70° C. Samples were then thawed, sonicated and titrated in Vero cells to determine the number of plaque forming units (pfu's) of virus produced by each culture.

As shown in FIG. 1, the number of pfu's produced in the control cultures infected with an moi of 1 increases rapidly for 24 hours then slows by 48 hours and 72 hours after infection. At this time, the system is exhausted, i.e., active virus has infected and destroyed not only those cells infected during the initial one hour of incubation but also those cells which became infected with virus released by the initially-infected cells. The lack of significant increase observed in the control cultures at 48 and 72 hours after treatment indicates that the virus production has peaked, due to the lack of viable cells in which to reproduce.

As shown in FIG. 1, treatment of cells with 50 μg/ml of resveratrol inhibited formation of infectious virus particles in pseudorabies virus infected cells by more than 99% at 24 hours. By 72 hours, infectious pseudorabies virus particles were virtually undetectable in cultures continuously incubated in the presence of 50 μg/ml of resveratrol.

EXAMPLE 2

Inhibiting Growth of *Neisseria gonorrhea* by Treatment with Resveratrol

Stock solutions of the resveratrol, obtained from Sigma Chemical Co, St. Louis, Mo. were prepared in 100% ethanol. Different quantities of the stock solution where added to melted chocolate agar which was then poured into a petri dish and allowed to solidify. The final concentration of resveratrol in the agar ranged from 1 μg to 200 μg/ml. The final concentration of ethanol in the agar was 0.5%. Control plates containing chocolate agar and ethanol at a final concentration of 0.5% were also prepared.

*Neisseria gonorrhea* was obtained from patients diagnosed with gonorrhea. The authenticity of the bacterium was confirmed utilizing standard microbiological techniques of identification. Cultures of the bacterial isolate were inoculated onto fresh plates and then 24 hours later, a suspension was made from isolated colonies.

10 μl aliquots of the suspension were spread evenly across the surface of samples of solidified control chocolate agar lacking resveratrol and samples of the chocolate agar containing resveratrol at final concentrations ranging from 1 to 200 μg/ml. Thereafter, the samples were incubated at 37° C. with or without 5% $CO_2$. All samples were visually examined for growth of the bacterium 24 hours later to determine the concentration of resveratol that inhibits growth by 50% ($MIC_{50}$) as well as the concentration which inhibits any visible growth ($MIC_{100}$)

EXAMPLE 3

Inhibiting Growth of *Neisseria meningiditis* by Treatment with Resveratrol

A culture of *Neisseria meningiditis* was obtained from the American Type Culture Collection. Authenticity of the bacterium was confirmed utilizing standard microbiological techniques of identification. Cultures of the bacterial isolate were inoculated onto fresh plates and then 24 hours later, a suspension was made from isolated colonies.

10 μl aliquots of the suspension were spread evenly across the surface of samples of solidified control chocolate agar lacking resveratrol and samples of the chocolate agar containing resveratrol at final concentrations ranging from 1 to 200 μg/ml. Thereafter, the samples were incubated at 37° C. with or without 5% $CO_2$. All samples were visually examined for growth of the bacterium 24 hours later to determine the resveratrol concentration that inhibits growth by 50% ($MIC_{50}$) and the resveratrol concentration which inhibits any visible growth ($MIC_{100}$)

Results

The results, shown in Table 1 below, demonstrate that resveratrol at a concentration of 25 μg/ml inhibited growth of *Neisseria gonorrhoeae* by 50%, while resveratrol at a concentration of 75 μg/ml inhibited growth of this pathogen by 100%. Resveratrol at a concentration of 100 μg/ml inhibited growth of *Neisseria meningiditis* by 50%, while resveratrol at a concentration of 125 μg/ml inhibited growth of this pathogen by 100%.

TABLE 1

The Inhibitory Concentration (IC) of Resveretrol on Bacteria and Yeast In Vitro

| Microorganism | $IC_{50}$μg/ml[a] | $IC_{100}$μg/ml[b] |
|---|---|---|
| *Neisseria gonorrhea* | 25 | 75 |
| *Neisseria meningitidis* | 100 | 125 |
| *Escherichia coli* | >200 | >200 |
| *Staphylococcus aureus* | >200 | >200 |
| Group A Beta Streptococcus | >200 | >200 |
| *Pseudomonas aeruginosa* | >200 | >200 |
| *Candida albicans* | >200 | >200 |

$IC_{50}$ is a 50% reduction in bacterial growth after 24 hours.
$IC_{100}$ is a complete inhibition of bacterial growth after 24 hours.

What is claimed is:

1. A method of treating a subject with a *Neisseria gonorrhea* or a *Neisseria meningiditis* infection of the eye, said method comprising administering 3,5,4'-trihydroxystilbene to the eye of the subject.

2. The method of claim 1, wherein the trans form of 3,5,4'-trihydroxystilbene is administered to the eye the subject.

3. The method of claim 1, wherein the cis form of 3,5,4'-trihydroxystilbene is administered to the eye of the subject.

4. A method of inhibiting or reducing infection with *Neisseria gonorrhea* in the urethra, genitalia, or cervix of a human subject, comprising:
    administering a pharmaceutical composition comprising resveratrol to the urethra, genitalia, cervix, or any combination thereof of said human subject.

5. The method of claim 4 wherein the pharmaceutical composition is administered to a mucous membrane of the subject.

6. The method of claim 4, wherein the composition comprises the trans form of resveratrol.

7. A method of treating a human subject infected with *Neisseria gonorrhea* comprising:
    administering a pharmaceutical composition comprising a therapeutically effective amount of resveratrol at an infected site of the subject.

8. The method of claim 7 wherein the pharmaceutical composition is administered via local administration to the genitalia, rectum, cervix, throat, oropharynx or any combination thereof of the subject.

9. The method of claim 7, wherein the composition comprises the trans form of resveratrol.

10. A method of inhibiting or reducing development of a *Neisseria meningiditis* infection in the eye of a neonate, comprising administering resveratrol to the eye of the neonate.

* * * * *